US00PP21714P2

(12) United States Plant Patent
Talmadge

(10) Patent No.: US PP21,714 P2
(45) Date of Patent: Feb. 15, 2011

(54) ***IPOMOEA* PLANT NAMED 'FNPALLIGR'**

(50) Latin Name: *Ipomoea batatas*
Varietal Denomination: Fnpalligr

(75) Inventor: Paul A. Talmadge, Orcutt, CA (US)

(73) Assignee: Floranova Service Corp., Lompoc, CA (US)

( * ) Notice: Subject to any disclaimer, the term of this patent is extended or adjusted under 35 U.S.C. 154(b) by 0 days.

(21) Appl. No.: 12/583,686

(22) Filed: Aug. 25, 2009

(51) Int. Cl.
*A01H 5/00* (2006.01)

(52) U.S. Cl. ..... Plt./258; Plt./373; Plt./263.1

(58) Field of Classification Search ..... Plt./263.1, Plt./373, 258
See application file for complete search history.

(56) References Cited

U.S. PATENT DOCUMENTS

| | | | | |
|---|---|---|---|---|
| PP17,505 | P3 * | 3/2007 | Lal et al. | Plt./258 |
| PP18,572 | P3 * | 3/2008 | Yencho et al. | Plt./258 |
| PP18,673 | P3 * | 4/2008 | Yencho et al. | Plt./258 |
| PP20,813 | P2 * | 3/2010 | Jandrew | Plt./263.1 |
| PP20,880 | P2 * | 3/2010 | Jandrew | Plt./263.1 |

* cited by examiner

*Primary Examiner*—Wendy C. Haas
(74) *Attorney, Agent, or Firm*—C. A. Whealy

(57) ABSTRACT

A new and distinct cultivar of *Ipomoea* plant named 'Fnpalligr', characterized by its compact, upright and mounding plant habit; freely branching habit and short internodes, dense and bushy growth habit; and medium to small light green-colored palmate-shaped leaves.

1 Drawing Sheet

Botanical designation: *Ipomoea batatas.*
Cultivar denomination: 'FNPALLIGR'.

BACKGROUND OF THE INVENTION

The present invention relates to a new and distinct cultivar of *Ipomoea* plant, botanically known as *Ipomoea batatas*, and hereinafter referred to by the name 'Fnpalligr'.

The new *Ipomoea* plant is a product of a planned breeding program conducted by the Inventor in Lompoc, Calif. The objective of the breeding program is to create new compact and freely branching *Ipomoea* cultivars with attractive foliage shape and coloration.

The new *Ipomoea* plant originated from an open-pollination during the autumn of 2007 of an unnamed proprietary selection of *Ipomoea batatas*, not patented, as the female, or seed, parent with an unknown selection of *Ipomoea batatas* as the male, or pollen, parent. The new *Ipomoea* was discovered and selected by the Inventor as a single plant within the progeny of the stated open-pollination in a controlled greenhouse environment in Lompoc, Calif. in March, 2008.

Asexual reproduction of the new *Ipomoea* plant by terminal cuttings in a controlled greenhouse environment in Lompoc, Calif. since April, 2008, has shown that the unique features of this new *Ipomoea* plant are stable and reproduced true to type in successive generations.

SUMMARY OF THE INVENTION

Plants of the new *Ipomoea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fnpalligr'.

These characteristics in combination distinguish 'Fnpalligr' as a new and distinct cultivar of *Ipomoea:*

1. Compact, upright and mounding plant habit.
2. Freely branching habit and short internodes, dense and bushy growth habit.
3. Medium to small light green-colored palmate-shaped leaves.

Plants of the new *Ipomoea* can be compared to plants of the female parent selection. Plants of the new *Ipomoea* differ from plants of the female parent selection in the following characteristics:

1. Leaves of plants of the new *Ipomoea* are more lobed than leaves of plants of the female parent selection.
2. Plants of the new *Ipomoea* have light green-colored leaves whereas plants of the female parent selection have dark purple-colored leaves.

Plants of the new *Ipomoea* can be compared to plants of the *Ipomoea batatas* 'Sweet Caroline Sweetheart Light Green', disclosed in U.S. Plant Pat. No. 18,572. In side-by-side comparisons conducted in Lompoc, Calif., plants of the new *Ipomoea* differed from plants of 'Sweet Caroline Sweetheart Light Green' in the following characteristics:

1. Plants of the new *Ipomoea* were more freely branching than plants of 'Sweet Caroline Sweetheart Light Green'.
2. Plants of the new *Ipomoea* had shorter internodes and were bushier and denser than plants of 'Sweet Caroline Sweetheart Light Green'.
3. Plants of the new *Ipomoea* had smaller leaves than plants of 'Sweet Caroline Sweetheart Light Green'.
4. Plants of the new *Ipomoea* had palmate-shaped leaves whereas plants of 'Sweet Caroline Sweetheart Light Green' had cordate-shaped leaves.

BRIEF DESCRIPTION OF THE PHOTOGRAPHS

The accompanying colored photographs illustrate the overall appearance of the new *Ipomoea* plant, showing the colors as true as it is reasonably possible to obtain in colored reproductions of this type. Colors in the photographs may differ slightly from the color values cited in the detailed botanical description which accurately describe the colors of the new *Ipomoea* plant.

The photograph at the bottom of the sheet comprises a side perspective view of typical plants of 'Fnpalligr' grown in a container.

The photograph at the top of the sheet comprises a close-up view of typical leaves of 'Fnpalligr'.

DETAILED BOTANICAL DESCRIPTION

The aforementioned photographs and following observations, measurements and values describe plants grown in Lompoc, Calif. in a polyethylene-covered greenhouse during the summer and under conditions which closely approximate commercial *Ipomoea* production. During the production of the plants, average day temperatures were 22° C. and average night temperatures were 17° C. Plants were grown in 15-cm containers and were six weeks old when the photographs and description were taken. In the detailed description, color references are made to The Royal Horticultural Society Colour Chart, 2007 Edition, except where general terms of ordinary dictionary significance are used.

Botanical classification: *Ipomoea batatas* 'Fnpalligr'.

Parentage:

- *Female, or seed, parent.*—Unnamed proprietary selection of *Ipomoea batatas*, not patented.
- *Male, or pollen, parent.*—Unknown selection of *Ipomoea batatas*, not patented.

Propagation:

- *Type.*—By terminal cuttings.
- *Time to initiate roots, summer.*—About four days at temperatures of 24° C.
- *Time to initiate roots, winter.*—About six days at temperatures of 18° C.
- *Time to produce a rooted young plant, summer.*—About twelve days at temperatures of 24° C.
- *Time to produce a rooted young plant, winter.*—About 18 days at temperatures of 18° C.
- Root description.—Thick, fleshy; white in color.
- *Rooting habit.*—Freely branching; moderately dense.
- *Tuber description.*—Tuber development has not been observed on plants of the new *Ipomoea*.

Plant description:

- *Plant habit.*—Compact, upright and mounding plant habit; freely branching habit and short internodes, dense and bushy habit; pinching is typically not required; vigorous growth habit and rapid growth rate.
- *Plant height.*—About 15 cm.
- *Plant diameter.*—About 40 cm.

Lateral branch description:

- *Quantity per plant.*—About eight lateral branches develop per plant.
- *Length.*—About 20 cm.
- *Diameter.*—About 5 mm.
- *Internode length.*—About 1.2 cm.
- *Strength.*—Strong.
- *Texture.*—Pubescent.
- *Color.*—Close to 145A.

Foliage description:

- *Arrangement.*—Alternate, simple.
- *Length.*—About 10.5 cm.
- *Width.*—About 9 cm.
- *Shape.*—Palmate.
- *Apex.*—Acuminate.
- *Base.*—Cordate.
- *Margin.*—Entire.
- *Texture, upper and lower surfaces.*—Smooth, glabrous.
- *Venation pattern.*—Palmate; arcuate.
- *Color.*—Developing leaves, upper surface: Close to N144A. Developing leaves, lower surface: Close to 145B. Fully expanded leaves, upper surface: Darker than 145A; venation, close to 145A. Fully expanded leaves, lower surface: Close to 148D; venation, close to 145C.
- *Petiole.*—Length: About 9.5 cm. Diameter: About 3 mm. Texture, upper and lower surfaces: Sparsely pubescent. Color, upper and lower surfaces: Close to 145B.

Flower description: Flower development has not been observed on plants of the new *Ipomoea*.

Temperature tolerance: Plants of the new *Ipomoea* have been observed to tolerate temperatures from about 5° C. to about 35° C.

Pathogen/pest resistance: Plants of the new *Ipomoea* have not been observed to be resistant to pests and pathogens common to *Ipomoea*.

It is claimed:

1. A new and distinct *Ipomoea* plant named 'Fnpalligr' as illustrated and described.

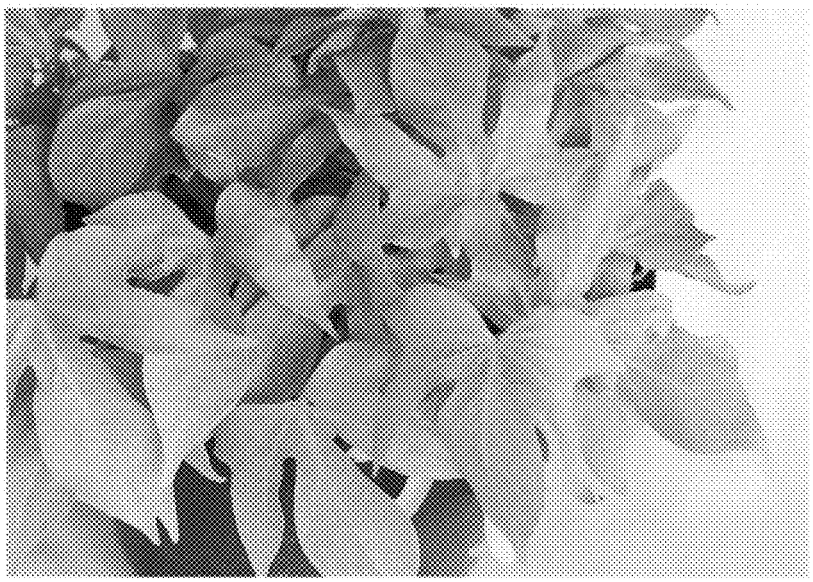
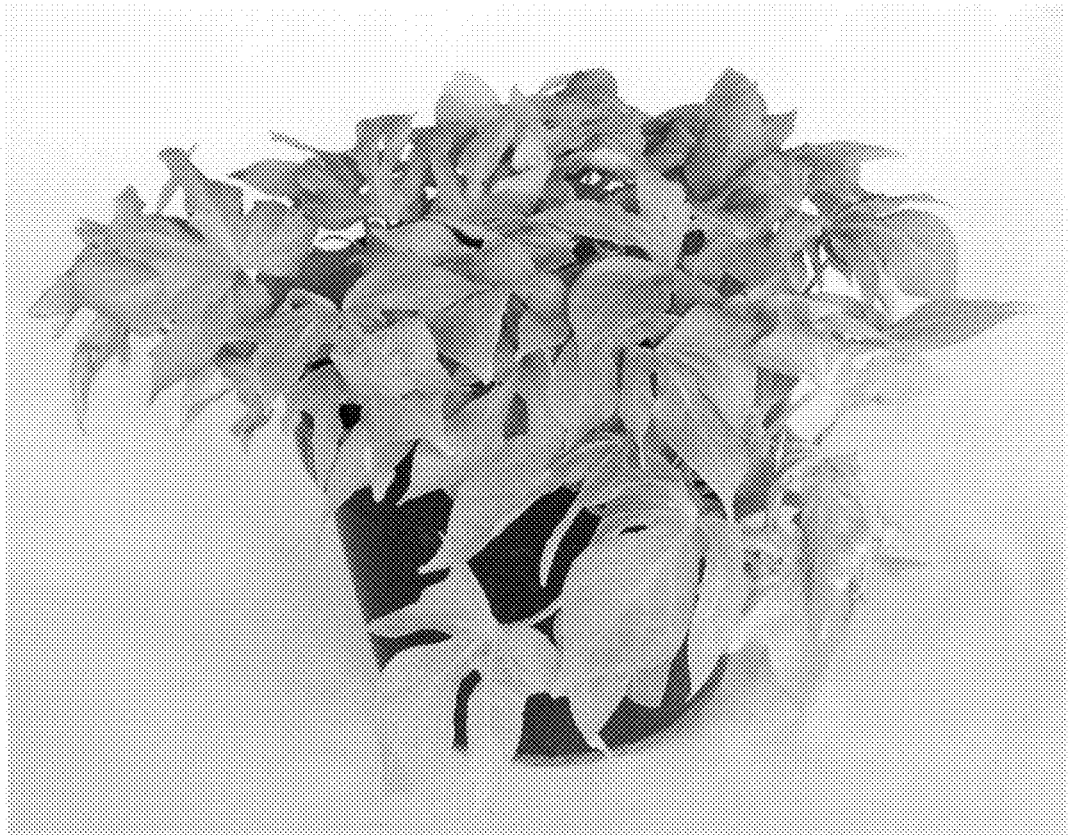

* * * * *